United States Patent
Bornzin et al.

(10) Patent No.: US 8,150,512 B2
(45) Date of Patent: Apr. 3, 2012

(54) USE OF IMPEDANCE TO ASSESS ELECTRODE LOCATIONS

(75) Inventors: Gene A. Bornzin, Simi Valley, CA (US); Peter Boileau, Valencia, CA (US); John W. Poore, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 638 days.

(21) Appl. No.: 12/273,286

(22) Filed: Nov. 18, 2008

(65) Prior Publication Data

US 2010/0125305 A1     May 20, 2010

(51) Int. Cl.
*A61N 1/00* (2006.01)

(52) U.S. Cl. .......................................... 607/8

(58) Field of Classification Search ............... 607/9, 27, 607/28, 547, 17, 18, 8
See application file for complete search history.

(56) References Cited

U.S. PATENT DOCUMENTS

| | | | |
|---|---|---|---|
| 5,466,254 A | 11/1995 | Helland | |
| 6,881,192 B1* | 4/2005 | Park | 600/529 |
| 2004/0030356 A1 | 2/2004 | Osypka | |
| 2008/0103541 A1 | 5/2008 | Osypka | |

FOREIGN PATENT DOCUMENTS

EP    1350539 A1    10/2003

* cited by examiner

*Primary Examiner* — Niketa Patel
*Assistant Examiner* — Mallika Fairchild

(57) ABSTRACT

A process for determining whether the location of a stimulation electrode meets a selected heart performance criteria includes providing stimulation to the heart through the electrode and obtaining an impedance measurement during stimulation delivery using an impedance sensing vector formed by electrodes that do not include the stimulation electrode. The impedance measurements are processed, either alone or in combination with an electrogram, also obtained during stimulation, to obtain a measure of hemodynamic performance.

17 Claims, 8 Drawing Sheets

US 8,150,512 B2

USE OF IMPEDANCE TO ASSESS ELECTRODE LOCATIONS

BACKGROUND OF THE INVENTION

1. Field of the Invention

The present invention relates to implantable cardiac stimulation devices, such as pacemakers and implantable cardioverter defibrillators (ICD) and, in particular, concerns a system and process involving the use of impedance signals to assess electrode locations, particularly during implant.

2. Description of the Related Art

Implantable cardiac stimulation devices, such as pacemakers and ICDs, are commonly used to treat heart abnormalities. Typically, these devices include a control unit and pulse generator positioned within a casing or can and a plurality of leads that extend from the can and into or over one or more of the chambers of the heart. When a heart abnormality, such as an arrhythmia, is detected, the control unit initiates therapy by causing the pulse generator to output electrical pulses or waveforms that are applied to the heart through electrodes on the leads. In order for therapy to be effective, the lead electrodes must be placed in the proper location.

The proper location, however, can vary significantly among patients. More specifically, the evoked response of a particular chamber can vary greatly depending on the position of the lead electrode with respect to the heart chamber. During implantation of the cardiac stimulation device, doctors often look at imagery to ascertain the physical location where the lead electrodes are being implanted. For example, doctors may attempt to implant the lead to position an electrode in the apex of the ventricle. Once the leads are implanted, the device is tested and therapeutic waveforms or pacing pulses are provided to the heart to verify the operation of the device.

Generally, at the implantation stage, a variety of different performance characteristics of the device are adjusted in order to provide a preferred level of operation. For example, the threshold for triggering the device to deliver a therapeutic impulse is adjusted and various delays between sensed events and the delivery of therapy are also adjusted so that the implanted device provides therapy to the patient at desired intervals. While various device parameters are generally adjusted or optimized to achieve a desired level of performance, there typically is not a lot of analysis, other than imaging the location of the implanted lead, to ensure that the lead electrode is positioned to provide a high or optimum level of therapy.

Consequently, while imaging of the lead during implantation provides a general indication that the lead electrode is in the correct location, it is possible that moving the lead electrode to a different location could result in an improved hemodynamic performance of the heart during therapy delivery. Hence, there is a need for a system and method that provides information regarding the hemodynamic performance of the heart during therapy so that an optimal lead electrode location may be determined during implant.

SUMMARY OF THE INVENTION

The aforementioned needs are satisfied by placing a lead of a cardiac stimulation device such that a stimulation electrode, i.e., an electrode through which electrical pulses will be applied to the heart, is positioned in a first location with respect to the heart and then inducing therapeutic stimulation to the heart via the stimulation electrode. The impedance of a region of the body, such as the thoracic cavity, is measured while stimulation is provided to the heart. The impedance measurement is made using a sensing vector that is defined by a set of electrodes that does not include the stimulation electrode. The impedance measurements are processed to determine a performance characteristic of the heart. The performance characteristic is evaluated to determine whether the location of the stimulation electrode provides a desired level of hemodynamic performance.

In one implementation, the hemodynamic performance characteristic is stroke volume which may be derived from multiple impedance measurements. In another implementation, the hemodynamic performance characteristic is cardiac output which is derived from the peak-to-peak changes in an impedance signal. In another implementation, the hemodynamic performance characteristic is contractility and isovolumic contraction time, which is derived from the time delay between the QRS peaks of an electrogram and the maximum derivative of admittance, i.e., the reciprocal of impedance. Yet another hemodynamic performance characteristic is relaxation time which is the time between the minimum derivative of admittance and the QRS complex. Yet another hemodynamic performance characteristic is the degree of synchrony which is the time between minimum and maximum derivatives of admittance.

By evaluating the impedance signal measured inside the patient's body, either alone or in combination with an electrogram, the hemodynamic performance of the heart during stimulation may be assessed. Thus, monitoring the impedance within the thoracic cavity for example, provides an indication as to how effective therapy, e.g., pacing stimulation, will be when it is delivered through an electrode at a particular location within, on, or adjacent the heart. This information can be used to select the position within, on, or adjacent the patient's heart that when stimulated, provides a desired level of hemodynamic performance. These and other objects and advantages of the present invention will become more apparent from the following description taken in conjunction with the accompanying drawings.

DETAILED DESCRIPTION OF THE PREFERRED EMBODIMENT

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
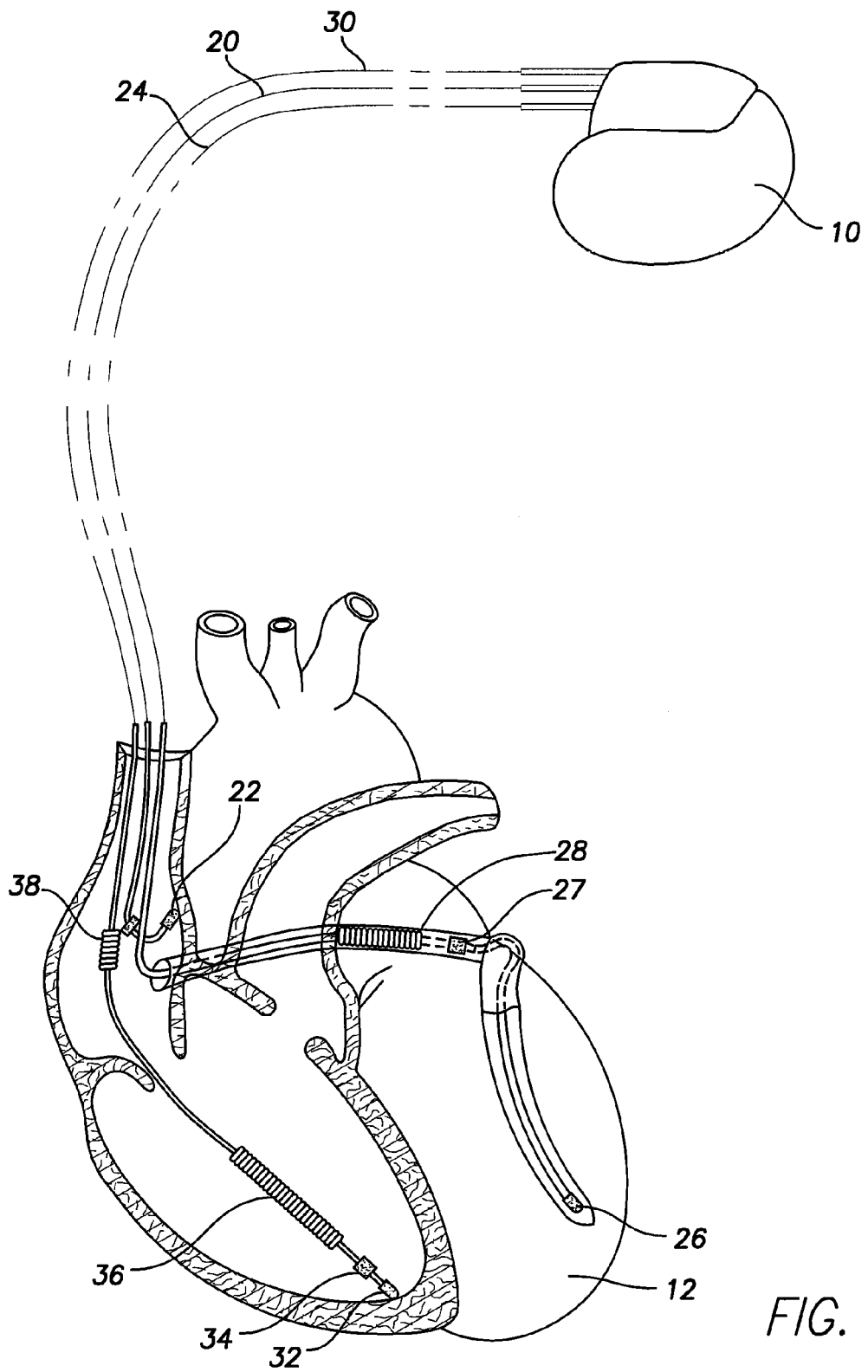
FIG. 1 is a simplified diagram illustrating an implantable stimulation device in electrical communication with at least three leads implanted in the patient's heart for delivering multi-chamber stimulation and shock therapy.

According to an embodiment shown in FIG. 1, there is an implanted pulse generator (IPG) 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the IPG 10 is coupled to an implantable right atrial lead 20 having an atrial tip electrode 22, which typically is implanted in the patient's right atrium, often in the atrial appendage but not limited to this position.

To sense left atrial and ventricular cardiac signals and to provide left chamber pacing therapy, the IPG 10 is coupled to a "coronary sinus" lead 24 designed for placement in the "coronary sinus region" via the coronary sinus is for positioning a distal electrode adjacent to the left ventricle and/or additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using a left ventricular tip electrode 26, left atrial pacing therapy using a left atrial ring electrode 27, and shocking therapy using a left atrial coil electrode 28. For a complete description of a coronary sinus lead, see U.S. Pat. No. 5,466,254, "Coronary Sinus Lead with Atrial Sensing Capability", which is hereby incorporated herein by reference.

The IPG 10 is also shown in electrical communication with the patient's heart 12 by way of an implantable right ventricular lead 30 having, in this embodiment, a right ventricular tip electrode 32, a right ventricular ring electrode 34, a right ventricular (VR) coil electrode 36, and an SVC coil electrode 38. Typically, the right ventricular lead 30 is transvenously inserted into the heart 12 so as to place the right ventricular tip electrode 32 in the right ventricular apex so that the VR coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle. The right ventricular tip electrode 32, however can be placed virtually any place in the right ventricle such as the mid-septal region or the right ventricular outflow tract and is not limited to the right ventricular apex.

While the IPG 10 is shown in this embodiment as having certain leads, according to other embodiments the IPG 10 may additionally or alternatively comprise other sensors and leads. For example, the IPG 10 may sense the electrical activity of a patient's heart 12 utilizing a multiple electrode lead having 8, 16, 32 or some other number of electrodes spatially distributed across at least one chamber of the heart 12. In some embodiments other sensors may be used such as pressure sensors, or the like.

Figure 2:
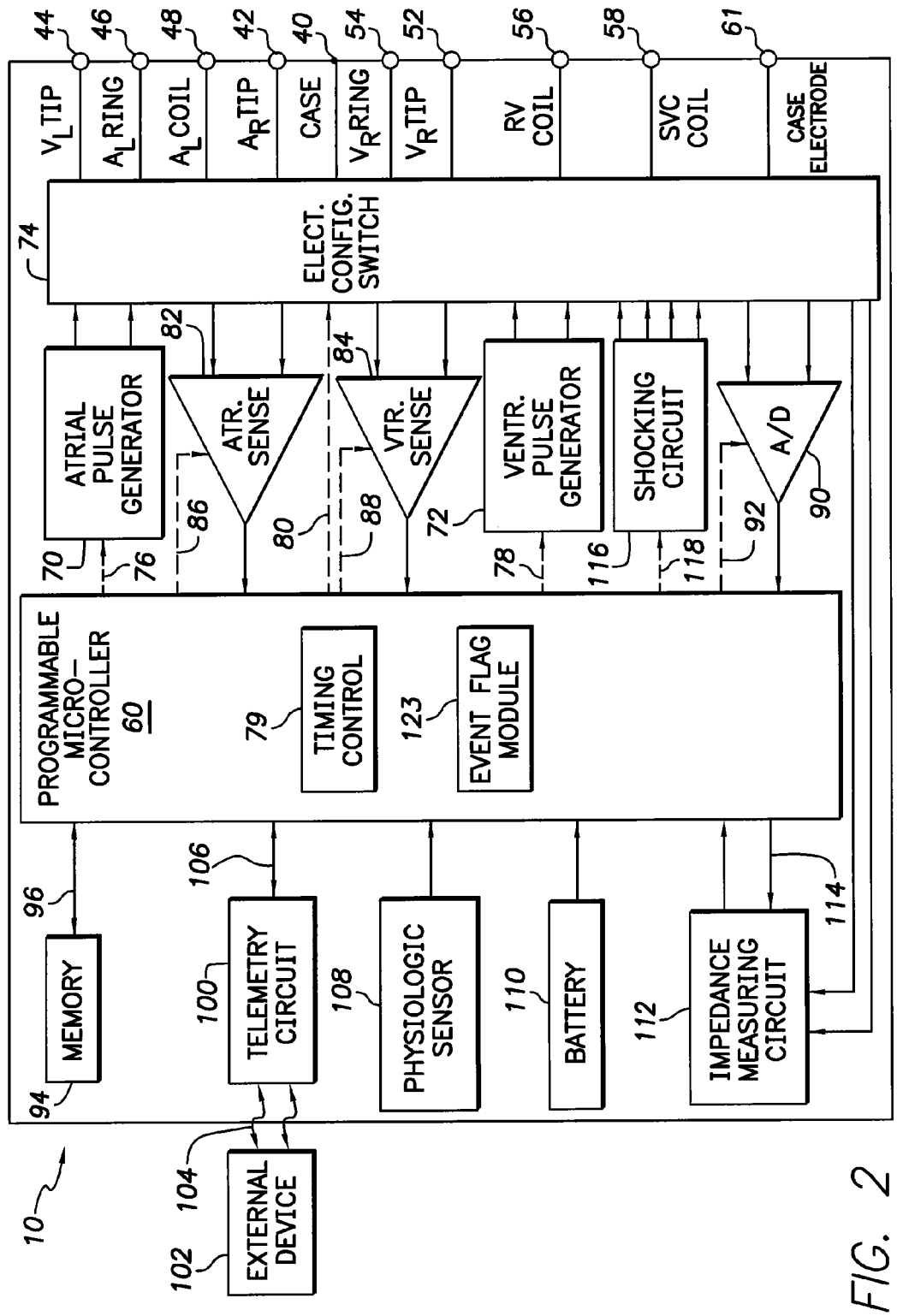
FIG. 2 is a functional block diagram of a multi-chamber implantable stimulation device of FIG. 1 illustrating the basic elements of a stimulation device which can provide cardioversion, defibrillation, and pacing stimulation.

With reference to FIG. 2, a simplified block diagram is shown of the multi-chamber IPG 10, which is capable of treating both fast and slow arrhythmias with stimulation therapy, such as cardioversion, defibrillation, and pacing stimulation. While a particular multi-chamber device is shown, this is for illustration purposes only, and one of skill in the art could readily duplicate, eliminate, or disable the appropriate circuitry in any desired combination to provide a device capable of treating the appropriate chamber(s) with cardioversion, defibrillation, and pacing stimulation. In certain embodiments of the invention, an implanted device may be utilized having appropriate circuitry for sensing the electrical activity of the heart without circuitry for providing stimulation therapy.

The housing 40 for the IPG 10, shown schematically in FIG. 2, is often referred to as the "can", "case", or "case electrode" and will act as the return electrode for "unipolar" modes. The housing 40 can further be used as a return electrode alone or in combination with one or more of the coil electrodes, 28, 36, and 38, for shocking purposes. The housing 40 further comprises a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector comprises a right atrial tip terminal ($A_R$ TIP) 42 adapted for connection to the atrial tip electrode 22.

To achieve left chamber sensing, pacing, and shocking, the connector comprises a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

As is also shown in FIG. 1, at least one additional electrode 61 can also be coupled to the case 40 of the IPG 10. As will be discussed in greater detail below, the at least one electrode 61 can obtain impedance measurements of the tissue adjacent the case 40. In general, the case 40 is implanted underneath the pectoral muscle and the impedance measurement obtained at this location is highly indicative of the stroke volume of the heart either as a result of an intrinsic heart beat or an evoked response.

To support right chamber sensing, pacing, and shocking, the connector further comprises a right ventricular tip terminal ($V_R$ TIP) 52, a right ventricular ring terminal ($V_R$ RING) 54, a right ventricular shocking terminal ($V_R$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the IPG 10 is a programmable microcontroller 60, which controls the various modes of stimulation therapy. As is well known in the art, the microcontroller 60 typically comprises a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 60 comprises the ability to process or monitor input signals (data) as controlled by a program code stored in a designated block of memory. The details of the design and operation of the microcontroller 60 are not critical to the present invention. Rather, any suitable microcontroller 60 can be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators 70, 72 can include dedicated, independent pulse generators, multiplexed pulse generators, or shared pulse generators. The pulse generators 70, 72 are controlled by the microcontroller 60 via appropriate control signals 76, 78 respectively, to trigger or inhibit the stimulation pulses.

The microcontroller 60 further comprises timing control circuitry 79 that is used to control the timing of such stimulation pulses (e.g., pacing rate, atrio-ventricular (AV) delay, inter-atrial conduction (A-A) delay, or inter-ventricular conduction (V-V) delay, etc.) as well as to keep track of the timing of refractory periods, PVARP intervals, noise detection windows, evoked response windows, alert intervals, marker channel timing, etc., which is well known in the art.

The switch 74 comprises a plurality of switches for connecting the desired electrodes to the appropriate I/O circuits, thereby providing electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 can also be selectively coupled to the right atrial lead 20, coronary sinus lead 24, and the right ventricular lead 30, through the switch 74 for detecting the presence of cardiac activity in each of the four chambers of the heart. Accordingly, the atrial and ventricular sensing circuits 82, 84 can include dedicated sense amplifiers, multiplexed amplifiers, or shared amplifiers. The switch 74 determines the "sensing polarity" of the cardiac signal by selectively closing the appropriate switches, as is also known in the art. In this way, the clinician can program the sensing polarity independent of the stimulation polarity.

Each sensing circuit 82, 84 preferably employs one or more low power, precision amplifiers with programmable gain and/or automatic gain control, bandpass filtering, and a threshold detection circuit, as known in the art, to selectively sense the cardiac signal of interest. The automatic gain control enables the IPG 10 to deal effectively with the difficult problem of sensing the low amplitude signal characteristics of atrial or ventricular fibrillation. The outputs of the atrial and ventricular sensing circuits 82, 84 are connected to the microcontroller 60 which, in turn, are able to trigger or inhibit the atrial and ventricular pulse generators 70, 72 respectively, in a demand fashion in response to the absence or presence of cardiac activity in the appropriate chambers of the heart. The sensing circuits 82, 84 in turn, receive control signals over signal lines 86, 88 from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the IPG 10 utilizes the atrial and ventricular sensing circuits 82, 84 to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation, which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardio version shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (EGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 can be coupled to the microcontroller, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection can occur on a beat-by-beat basis or on a sampled basis. Preferably, a capture threshold search is performed once a day during at least the acute phase (e.g., the first 30 days) and less frequently thereafter. A capture threshold search would begin at a desired starting point (either a high energy level or the level at which capture is currently occurring) and decrease the energy level until capture is lost. The lowest value at which there is consistent capture is known as the capture threshold. Thereafter, a safety margin or a working margin is added to the capture threshold.

The microcontroller 60 is further coupled to a memory 94 by a suitable data/address bus 96, wherein the programmable operating parameters used by the microcontroller 60 are stored and modified, as required, in order to customize the operation of the IPG 10 to suit the needs of a particular patient. Such operating parameters define, for example, pacing pulse amplitude, pulse duration, electrode polarity, rate, sensitivity, automatic features, arrhythmia detection criteria, and the amplitude, waveshape, and vector of each shocking pulse to be delivered to the patient's heart 12 within each respective tier of therapy. An embodiment of the invention senses and stores a relatively large amount of data (e.g., from the data acquisition system 90), which data can then be used for subsequent analysis to guide the programming of the IPG 10.

Advantageously, the operating parameters of the IPG 10 can be non-invasively programmed into the memory 94 through a telemetry circuit 100 in telemetric communication with the external device 102, such as a remote monitoring unit, programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the IPG 10 (as contained in the microcontroller 60 or memory 94) to be sent to the external device 102 through an established communication link 104.

In the preferred embodiment, the IPG 10 further comprises a physiologic sensor 108, commonly referred to as a "rate-responsive" sensor because it is typically used to adjust pacing stimulation rate according to the exercise state of the patient. However, the physiological sensor 108 can further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators 70 72 generate stimulation pulses. While shown as being included within the IPG 10, it is to be understood that the physiologic sensor 108 can also be external to the IPG, yet still be implanted within or carried by the patient. A common type of rate responsive sensor is an activity sensor, such as an accelerometer or a piezoelectric crystal, which is mounted within the housing 40 of the IPG 10. Other types of physiologic sensors are also known, for example, sensors that sense the oxygen content of blood, respiration rate and/or minute ventilation, pH of blood, ventricular gradient, etc. However, any sensor can be used that is capable of sensing a physiological parameter that corresponds to the exercise state of the patient. The type of sensor used is not critical and is shown only for completeness.

The stimulation device additionally comprises a battery 110, which provides operating power to the circuits shown in FIG. 2, including telemetry circuit 100. For the IPG 10, which employs shocking therapy, the battery 110 is capable of operating at low current drains for long periods of time, and then be capable of providing high-current pulses (for capacitor charging) when the patient requires a shock pulse. The battery 110 also has a predictable discharge characteristic so that elective replacement time can be detected. Accordingly, the IPG 10 preferably employs lithium/silver vanadium oxide batteries.

The IPG 10 further comprises magnet detection circuitry (not shown), that is coupled to the microcontroller 60. It is the purpose of the magnet detection circuitry to detect when a magnet is placed over the IPG 10, which magnet can be used by a clinician to perform various test functions of the IPG 10 and/or to signal the microcontroller 60 that the external programmer 102 is in place to receive or transmit data to the microcontroller 60 through the telemetry circuits 100. However, the magnet detection circuitry is not necessary to establish a communication link 104 according to some embodiments. In certain embodiments, the magnetic detection circuitry may trigger specific behavior such as signaling the status of the battery 110 or storing an electrogram.

As further shown in FIG. 2, the IPG 10 is shown as having an impedance measuring circuit 112, which is enabled by the microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode can be used. As will also be discussed in greater detail below, the impedance measurement circuit 112 can also be used to measure impedance as an indication of the stroke volume of the heart. This measurement, at implantation, allows the implanting physician to evaluate stroke volume when selecting the implant site for the leads in the manner that will be discussed in greater detail below.

In the case where the IPG 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5-10 Joules), or high energy (11 to 40 Joules), as controlled by the microcontroller 60. Such shocking pulses are applied to the patient's heart 12 through at least one shocking electrode but potentially more shocking electrodes, and as shown in this embodiment, selected from the left atrial coil electrode 28, the RV coil electrode 36, and/or the SVC coil electrode 38. As noted above, the housing 40 can act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to conserve battery life), and/or synchronized with an R-wave and/or pertaining to the treatment of tachycardia. Defibrillation shocks are generally of moderate to high energy level (i.e., corresponding to thresholds in the range of 5-40 Joules), and pertaining to the treatment of fibrillation. Accordingly, the microcontroller 60 is capable of controlling the synchronous or asynchronous delivery of the shocking pulses.

Microcontroller 60 of the IPG 10 further comprises an event flag module 123. As discussed below, flag 123 can be set by an external device 102 in order to indicate that the external device 102 has downloaded data contained in the memory 94 of microcontroller 60. When the external device 102 sets the flag 123, the flag 123 may correspond to an enabled condition and in some embodiments a logical "1" value. The microcontroller 60 is further configured in some embodiments to set the flag 123 when an event has occurred to a disabled condition, corresponding in some embodiments to a logical "0" value. The use of a particular electrical value or signal for each condition of the flag may, of course, be varied depending on a particular design choice. In some embodiments, flag 123 includes multiple flags corresponding to a variety of indicators for indicating different events or conditions. As will be explained in more detail below, the flag 123 may therefore be used in some embodiments to indicate when a remote monitoring unit should download data from the IPG 10.

Figure 3:
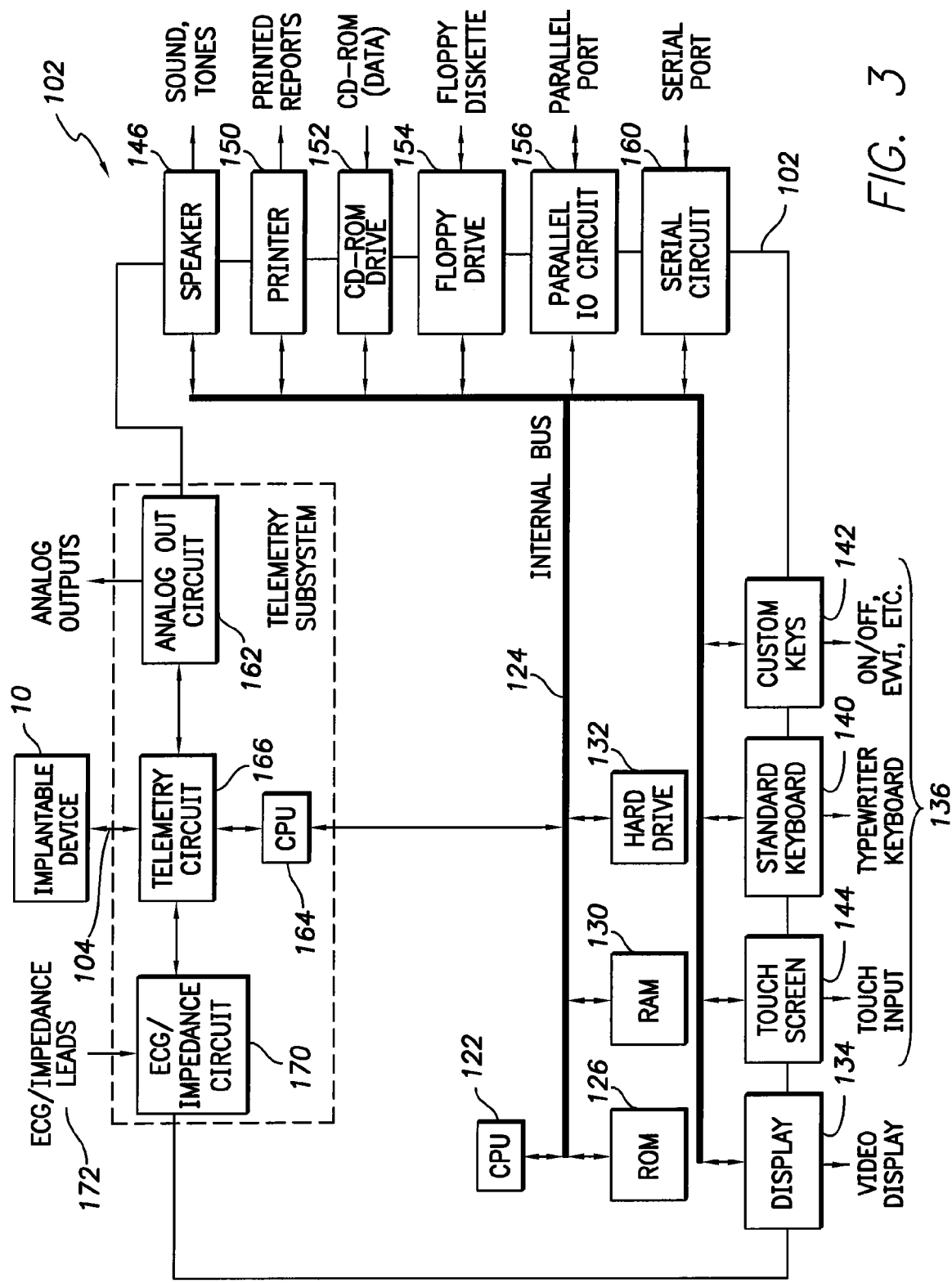
FIG. 3 is a functional block diagram of a programmer that communicates with the multi-chamber implantable stimulation device of FIG. 1.

FIG. 3 is a functional block diagram of one embodiment of the external device 102, such as a physician's programmer or remote monitoring unit or pacing system analyzer (PSA). The external device 102 comprises a CPU 122 in communication with an external bus 124. The internal bus 124 provides a common communication link and power supply between various electrical components of the external device 102, such as the CPU 122. The external device 102 also comprises memory and data storage such as ROM 126, RAM 130, and a hard drive 132 commonly in communication with the internal bus 124. The ROM 126, RAM 130, and hard drive 132 provide temporary memory and non-volatile storage of data in a well known manner. In one embodiment, the ROM 126, RAM 130, and hard drive 132 can store control programs and commands for upload to the IPG 10 as well as operating software for display of data received from the IPG 10. It will be appreciated that in certain embodiments alternative data storage/memory devices, such as flash memory, can be included or replace one or more of the ROM 126, RAM 130, and hard drive 132 without detracting from the spirit of the invention.

The external device 102 also comprises a display 134. The display 134 is adapted to visually present graphical and alphanumeric data in a manner well understood in the art. The external device 102 also comprises input devices 136 to enable a user to provide commands and input data to the external device 102. In one embodiment, the input devices 136 include a keyboard 140, a plurality of custom keys 142, and a touch screen 144 aspect of the display 134. The keyboard 140 facilitates entry of alphanumeric data into the external device 102. The custom keys 142 are programmable to provide one-touch functionality of predefined functions and/or operations. The custom keys 142 can be embodied as dedicated touch keys, such as associated with the keyboard 140 and/or predefined areas of the touch screen 144. In this embodiment, the external device 102 also comprises a speaker 146 and a printer 150 in communication with the internal bus 124. The speaker 146 is adapted to provide audible alert send signals to a user. The printer 150 is adapted to provide a printed readout of information from the external device 102.

In this embodiment, the external device 102 also comprises a CD drive 152 and a floppy drive 154 which together provide removable data storage. In this embodiment, the external device also comprises a parallel input-output (IO) circuit 156, a serial IO circuit 160, and an analog output circuit 162. In certain embodiments, the external device 102 also comprises a USB interface. In some embodiments, the external device 102 may also comprise an industry standard interface compatible with other portable storage devices such as a flash memory device. These circuits 156, 160, 162 provide a variety of communication capabilities between the external device 102 and other devices in a manner well understood in the art.

The external device 102 also comprises an electrocardiogram (ECG) or impedance circuit 170 in communication with a plurality of ECG or impedance leads 172. The ECG or impedance circuit 170 and the ECG or impedance leads 172 obtain electrical signals from the surface of a patient's body and configure the signals for display as an ECG waveform on the display 134 of the external device 102 or provide impedance measurements that can be used to determine the stroke volume or other related parameters of the heart to select the best implantation site of the electrodes in the manner that will be described in greater detail herein below.

The external device 102 also comprises a telemetry CPU 164 and a telemetry circuit 166, which establish the telemetric link 104 in cooperation with the IPG 10. The telemetric link 104 comprises a bidirectional link to enable the external device 102 and the IPG 10 to exchange data and/or commands. As previously noted, the establishment of the telemetric link 104 is in certain embodiments facilitated by a wand or programmer head, which is placed in proximity to the IPG 10. The wand or programmer head facilitates establishment of the telemetric link 104 by placing an antenna structure in a closer proximity to the IPG 10 to facilitate conduction of transmitted signals to the external device 102.

The telemetric link 104 can in some embodiments comprise a variety of communication protocols appropriate to the needs and limitations of a given application. In certain embodiments, the telemetric link 104 comprises radio frequency (RF) telemetry. In one particular embodiment, the telemetric link 104 comprises a frequency modulated digital communication scheme wherein logic ones are transmitted at a first frequency A and logic zeros are transmitted second frequency B. As the IPG 10 is powered by a battery having limited capacity and in certain embodiments the external device 102 is powered by line voltage, e.g., not subject to the stringent power limitations of the IPG 10, the bidirectional telemetric link 104 can proceed in an asymmetric manner. For example, in one embodiment, a transmission power and data rate from the external device 102 to the IPG 10 via the telemetric link 104 can proceed at higher power levels and/or higher data transmission rates than the reciprocal data rates and transmission power from the IPG 10 to the external device 102. The telemetry circuit 100 of the IPG 10 as well as the telemetry circuit 166 and CPU 164 of the external device 102 can select or be adjusted to provide a desired communication protocol and transmission power. In some circumstances, the external device 102 is adapted to function as a pacing system analyzer (PSA) which is used by implanting physicians to set the parameters of the implanted device and to observe the performance of the implanted device. In this way, the implanting physician can dynamically observe and change the operational characteristics of the device so that the device is providing therapy to the patient at a desired level.

With reference to FIG. 1, a plurality of internal electrodes may be positioned in, on, or adjacent the heart of the patient. To this end, intracardiac electrodes 22, 26, 27, 28, 32, 34, 36, 38 may be placed within the chambers of the heart or over chambers of the heart via coronary veins. Subcutaneous electrodes, such as the casing 10 itself or a temporary electrode in the area adjacent the casing pocket, e.g., underneath the pectoral muscle, where the case will be implanted, may be placed. Intravascular electrodes may also be place in areas of the vasculature outside of the heart, such as the inferior vena cava (IVC) or above the superior vena cava (SVC) in the brachiocephalic vein, using a temporary implantable lead. These internal electrodes may be used to define various impedance sensing vectors for obtaining impedance measurements occurring either simultaneously with or shortly after the delivery of therapy to the heart 12. Exemplary sensing vectors formed using internal electrodes include atrial tip electrode 22 to case 40 or pocket, SVC coil electrode 38 to case 40, atrial tip electrode 22 to IVC electrode (not shown) and SVC coil electrode to IVC electrode. As will be discussed in greater detail below, the transthoracic impedance provides an indication as to the stroke volume or other performance characteristics of the heart that occurs as a result of delivering stimulation to the heart.

By evaluating the transthoracic impedance, the placement of the electrode, e.g., the ventricular pacing electrodes 26, 32 or the atrial pacing electrode 22, 27 can be evaluated to determine whether the current electrode position provides an evoked response having a corresponding stroke volume or other performance parameter at a desired level. Thus, an implanting physician can evaluate the placement of the electrodes and adjust the placement of the electrodes while observing a signal indicative of the stroke volume of the heart or other performance characteristics of the heart at the various different locations during implantation. The implanting physician can preferably select locations for each of the electrodes that result in more optimal performance of the heart in response to receiving stimulation from the implantable stimulation device 10.

Figure 4:
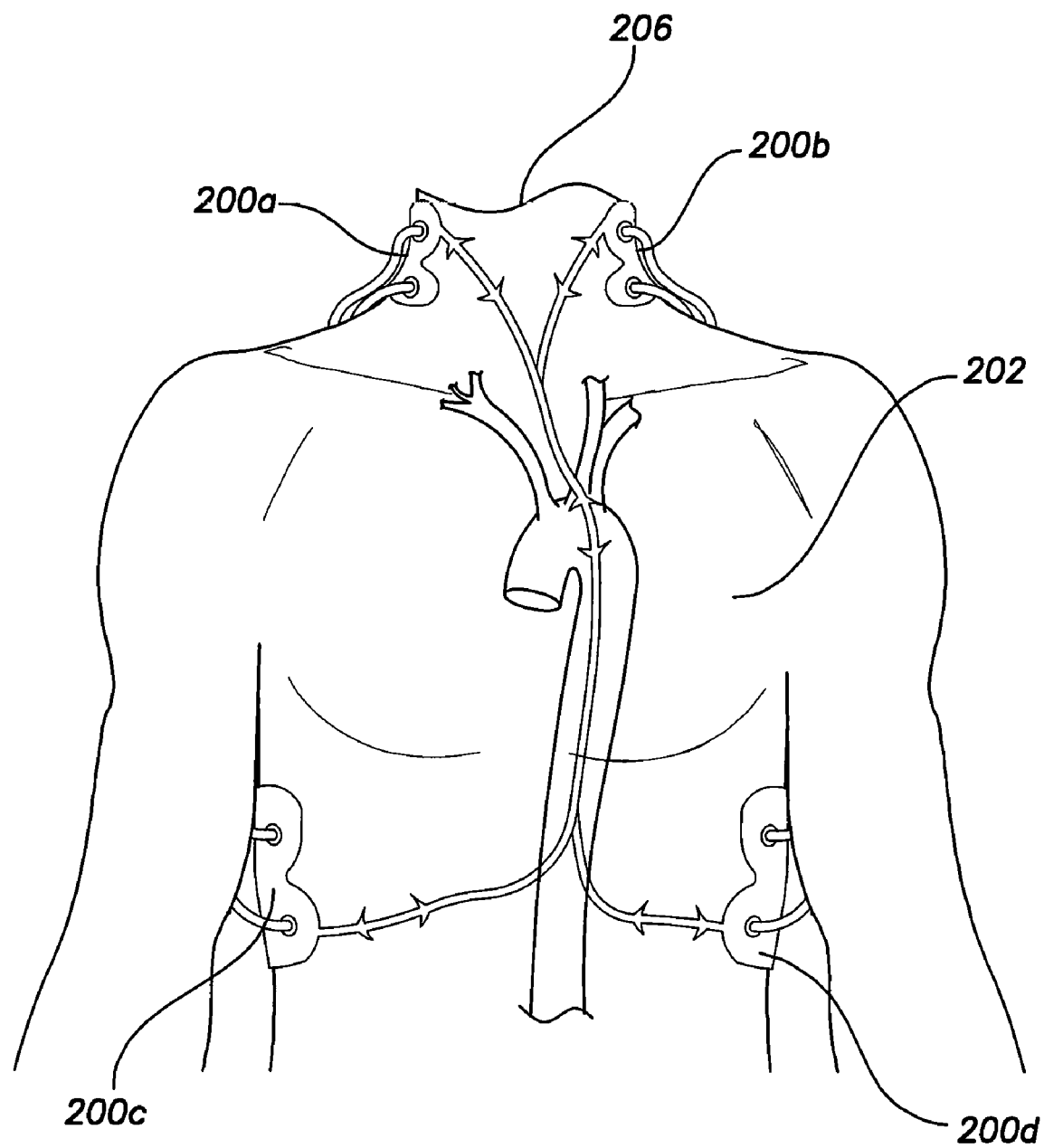
FIG. 4 is an exemplary configuration of external electrodes that can be used to sense impedance within the thoracic cavity of a patient and provide such impedance information to the programmer of FIG. 3.

In addition to the intracardiac electrodes, additional exterior electrodes may be positioned on the body to measure transthoracic impedance in the manner shown in FIG. 4. As shown in FIG. 4, a plurality of electrodes 200a, 200b, 200c, 200d are positioned on the torso 202 of the patient and various lead paths 204 between the sets of leads provide measurements of transthoracic impedance.

As shown in FIG. 4, the electrodes 200 can be positioned on either side of the neck 206 of the patient and at either side of the torso 202. These positions of electrodes are, of course, simply exemplary, but it will be appreciated that, by placing the electrodes at spaced and distal areas of the thoracic cavity, a plurality of different vectors between electrodes 200 can be established. The plurality of different vectors can thus be used to determine impedance along different vectors which can provide more detailed information of the stroke volume or performance of the heart in response to a received therapeutic stimulation or waveform. The leads can then be coupled to the PSA 102 via the ECG/impedance circuit 170 in the manner illustrated. Thus, the PSA 102 can provide an indication of transthoracic impedance as a result of delivery of a stimulation pulse to the heart from either signals measured with the leads of the implanted device 10 that are provided to the PSA 102 via the telemetry circuit 166 or can provide the transthoracic impedance signals measured by the external electrodes 172 in a manner that is known in the art or can be measured using some combination of implanted and external electrodes.

Impedance measurements may also be obtained using a sensing vector that is defined by an internal electrode and an external electrode. For example, one of the atrial tip electrode 22 (FIG. 1) and SVC coil electrode 38 may be used in combination with external electrode 200d (FIG. 4) to measure transthoracic impedance.

In general, it is desirable to measure the transthoracic impedance using a sensing vector that is defined by electrodes that are fixed in position with respect to the electrode that has been positioned for stimulation. The positioned electrode will measure different impedance based on its location. Accordingly, impedance is preferably measured independent of the electrode that has been positioned. As described above, the impedance sensing vector may be defined by one or more of external electrodes and internal electrodes, e.g., intracardiac electrodes, subcutaneous electrodes and intravascular electrodes; or the combination of any two types, e.g., internal electrode to external electrode. Such vectors provide an impedance measurement that is independent of the location of the electrode that is being used to delivery therapy. Consequently, a more consistent measurement of the transthoracic impedance can be obtained.

In one implementation, the external electrodes 200 may be used to measure the transthoracic impedance resulting from stimulation pulses delivered by a first implanted electrode. Subsequently, after an optimal location of the first implanted electrode is found and the first electrode is positioned in place, the first implanted electrode can be used to define the impedance measurement vector with respect to other electrodes. It will be appreciated from the following discussion that any of a number of different electrode combinations can be used to measure the transthoracic impedance which can then be used as an indication of the stroke volume occurring as a result of the evoked response of the chamber of the heart being stimulated.

Figure 5:
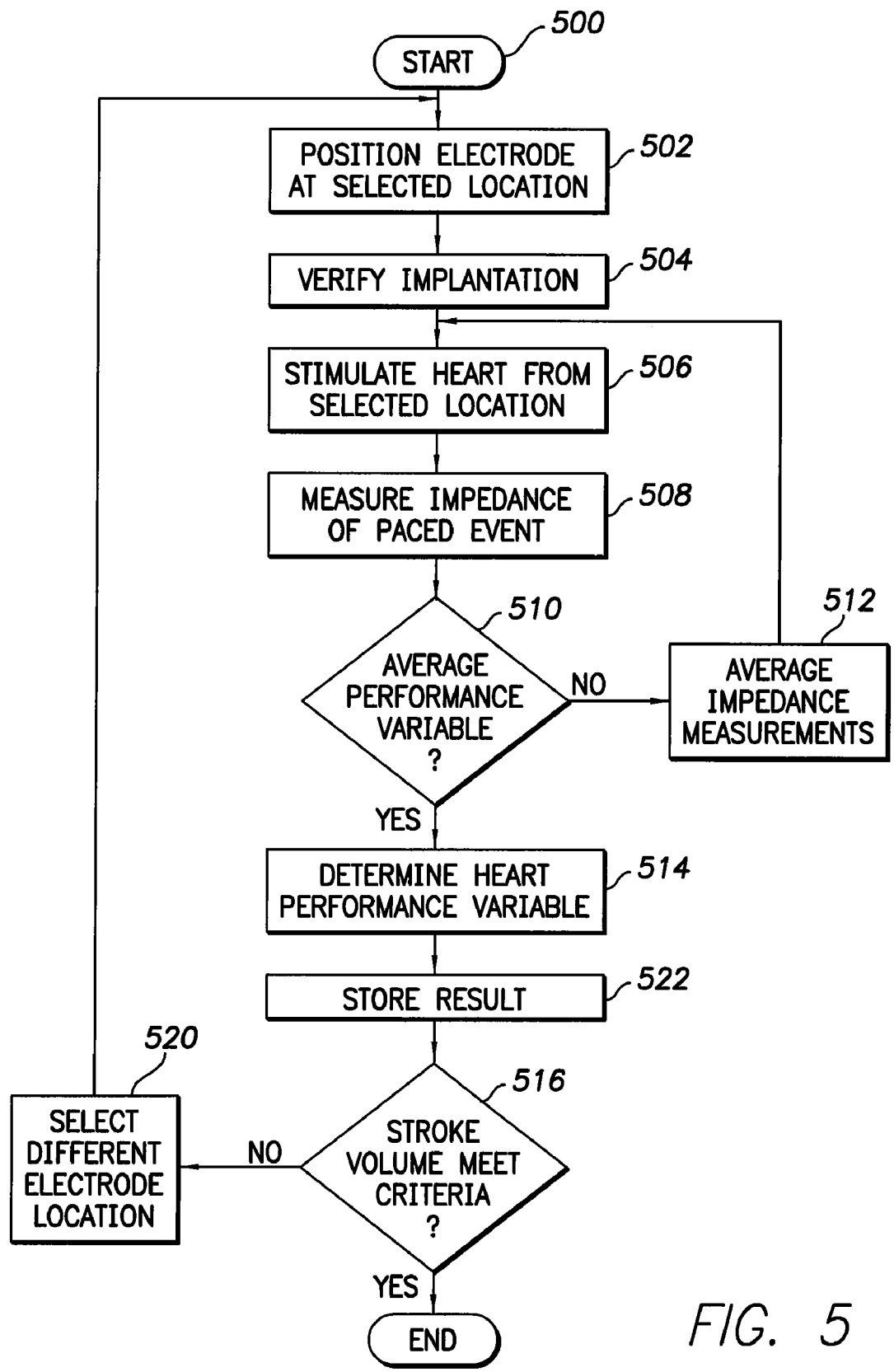
FIG. 5 is an exemplary flowchart illustrating a process whereby impedance measurements obtained through one or more electrodes can be used to assess the stroke volume of the heart in response to stimulation being provided by the implantable stimulation device with the leads located at a selected location.

An exemplary process 500 for assessing the hemodynamic performance brought about by stimulation delivered by an electrode positioned at a selected location is shown in the flowchart of FIG. 5. At state 502, a "stimulation electrode" is positioned at a selected location with respect to the chamber of the heart. The exact placement of the stimulation electrode is dependent on the type of lead and the general area that is believed to provide the best evoked response of the chamber of the heart. For example, pacing leads in the right and left ventricles are generally placed to position a tip electrode in the apex of the ventricle as this is generally known to provide the best pacing location for evoking a paced response by the heart. However, given the morphology of different patients this may not be the best position for all patients. Once the stimulation electrode is placed at a selected location in state 502, the physician may verify the position in state 504 in a number of different ways. For example, imaging technology, such as ultrasound, may be used to ensure that the stimulation electrode is positioned at a desired location of the heart.

In state 506, once the stimulation electrode position has been verified, the programmer 102 may stimulate the heart using the stimulation electrode. In state 508, while the heart is being stimulated, impedance values in the thoracic cavity are measured using other electrodes. Impedance measurements taken during stimulation pulse delivery may be susceptible to noise resulting from stimulation artifacts. Accordingly, in order to obtain a less noisy impedance signal, impedance measurements are preferably blanked, i.e., not taken, at the time of delivery of each stimulation pulse.

Figure 6A:
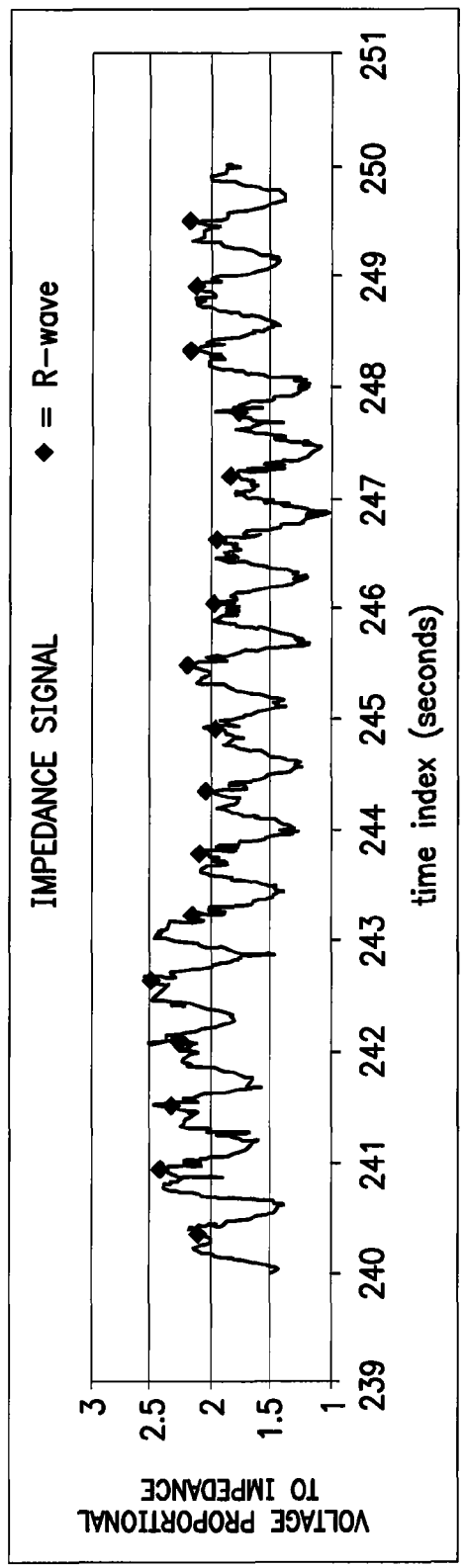
FIGS. 6A and 6B are exemplary impedance waveforms illustrating the features that can be evaluated by the stimulation device.
Figure 6B:
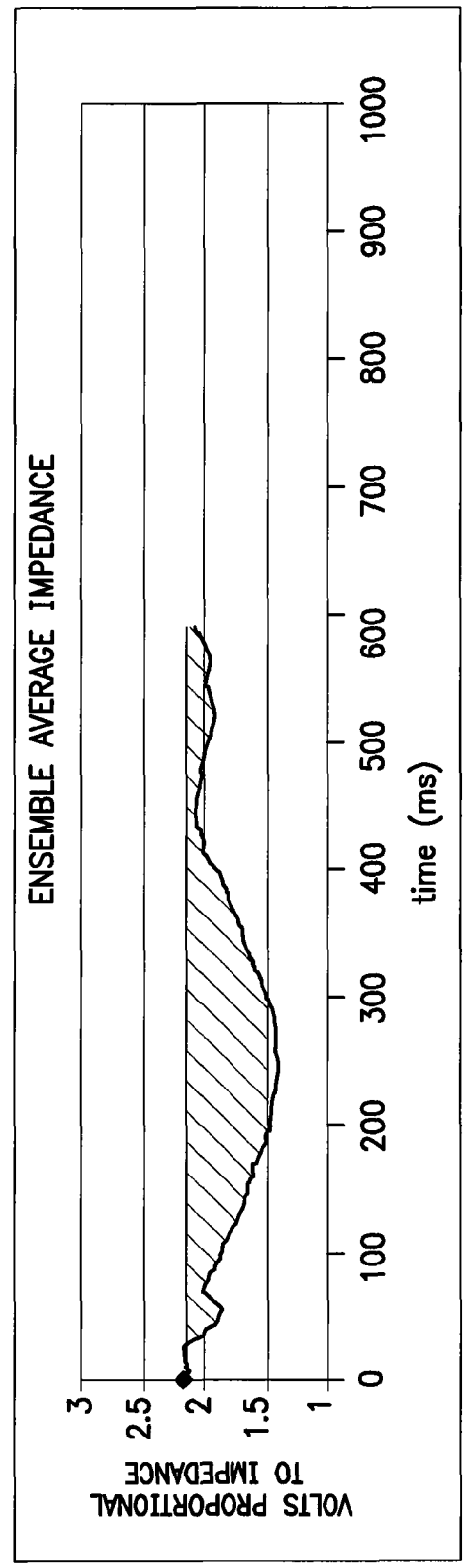

In decision state 510, it is determined whether a sufficient number of impedance measurements have been made in order to have an accurate assessment of a performance variable or characteristic. Generally, a series of stimulations are provided over a period of time. Once a sufficient number of impedance measurements have been made, the stimulations can then cease. In one implementation that is graphically represented in FIGS. 6A and 6B, a plurality of stimulations are provided to the heart resulting in a plurality of evoked responses, each including an R-wave. Voltage measurements are made over time and an ensemble average impedance is developed for the particular implantation location. This type of measurement provides an indication of the stroke volume of the heart in response to stimulation being provided at the stimulation electrode location.

As shown in FIG. 5, impedance measurements are obtain in state 506 and averaged in state 512 until it has been determined in decision state 510 that enough data has been collected to assess the performance variable of the heart in response to stimulations being provided at the stimulation electrode location. In state 514, the performance variable parameter is determined and in decision state 516 it is determined whether the parameter meets a desired criteria. In state 520, if the parameter does not meet the desired criteria, a new location is selected for the stimulation electrode and the process is repeated. In this way, the physician can determine which location for the stimulation electrode provides the best hemodynamic response.

Alternatively, in state 522 the measured criteria can be stored and the physician can then, in state 520, switch to the new stimulation location. By storing the data, the physician can compare results between different stimulation locations before finalizing a desired stimulation electrode location.

While the process of FIG. 5 is generally directed toward assessing the position of a single stimulation electrode, the process may be expanded to multiple site stimulation positions, as in the case of bi-ventricular pacing. This process involves positioning a first left-ventricular (LV) stimulation electrode at a first location with respect to the LV, such as the coronary sinus, and a first right-ventricular (RV) stimulation electrode at a first location with respect to the RV, such as the RV apex. Impedance measurements of the transthoracic cavity are obtained while bi-ventricular stimulation pulses are being delivered to the patient's heart through the RV and LV electrodes. As before, these impedance measurements are obtained using a sensing vector that does not include either of the first LV electrode and the first RV electrode. The impedance measurements are assessed to ascertain whether a heart performance parameter satisfies a hemodynamic criteria.

If the criteria is not satisfied, a different stimulation location may be selected for one or both of the RV stimulation electrode and LV stimulation electrode. The different stimulation location may be accessed by moving the relevant stimulation electrode to the new location. For example, in a case of a bi-polar RV lead with a tip electrode positioned in the RV apex and a bipolar LV lead, the RV electrode may remain at the same location, while the LV is moved to position the tip electrode at the new stimulation location. Alternatively, the RV electrode may be moved while the LV electrode remains in the same location.

In the case of a multi-electrode arrangement provided by a multi-electrode lead, the different stimulation location may be accessed by selecting the electrode closest to the new location. For example, in a case of a bi-polar RV lead with a tip electrode positioned in the RV apex and a multi-polar LV lead having multiple electrodes along the coronary veins, the RV electrode may remain at the same location, while the LV electrode closest to the stimulation location is selected as the stimulation electrode.

Figure 7A:
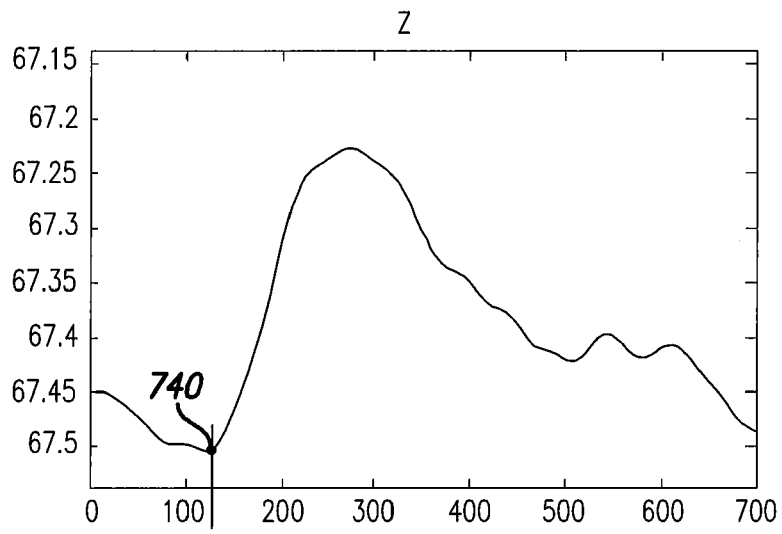
FIGS. 7A, 7B and 7C are respective transthoracic impedance (Z), transthoracic impedance derivative (dZ/dt) and IEGM waveforms obtained during pacing stimulation through a stimulation electrode at a first stimulation location.
Figure 7B:
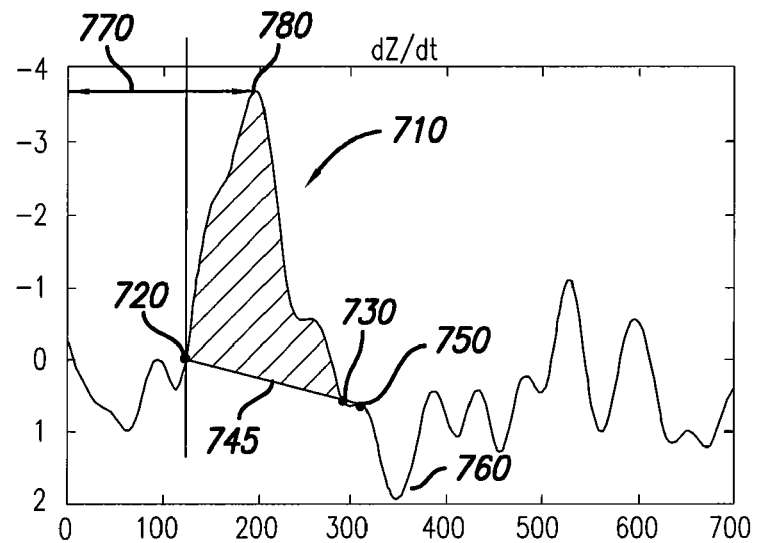
Figure 7C:
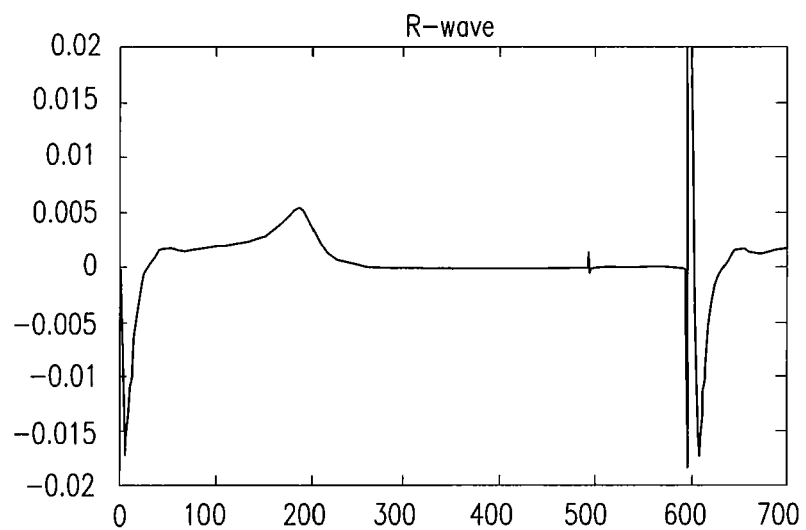
Figure 8A:
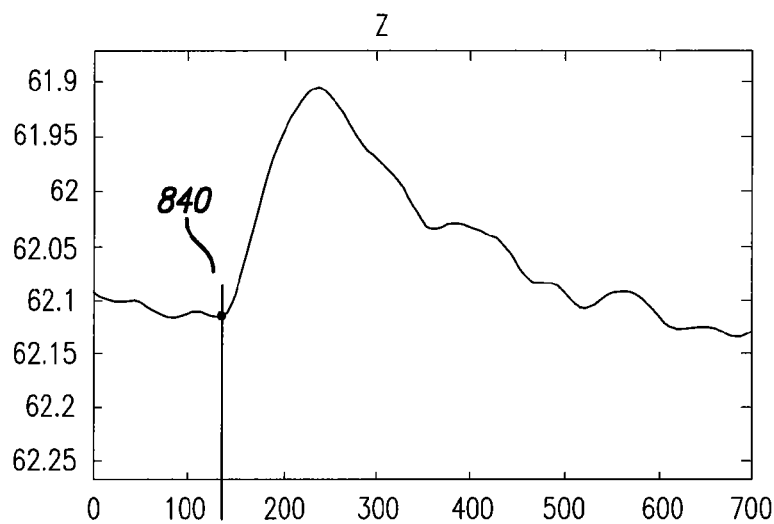
FIGS. 8A, 8B and 8C are respective transthoracic impedance (Z), transthoracic impedance derivative (dZ/dt) and IEGM waveforms obtained during pacing stimulation through a stimulation electrode at a second stimulation location.
Figure 8B:
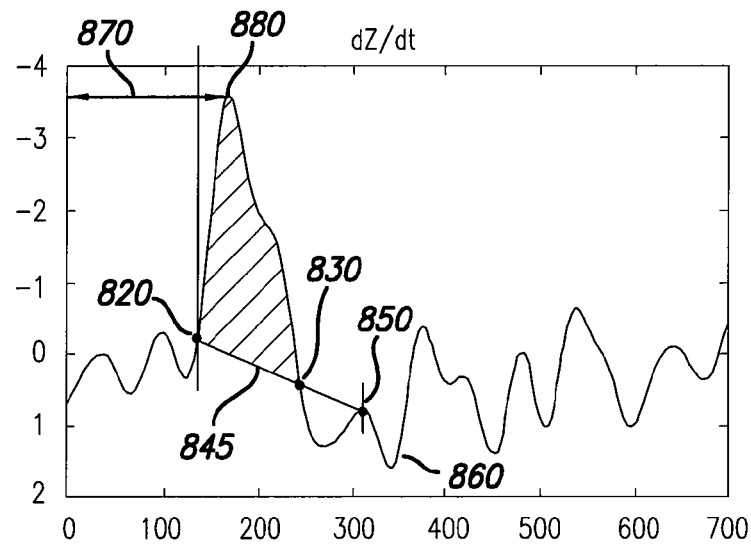
Figure 8C:
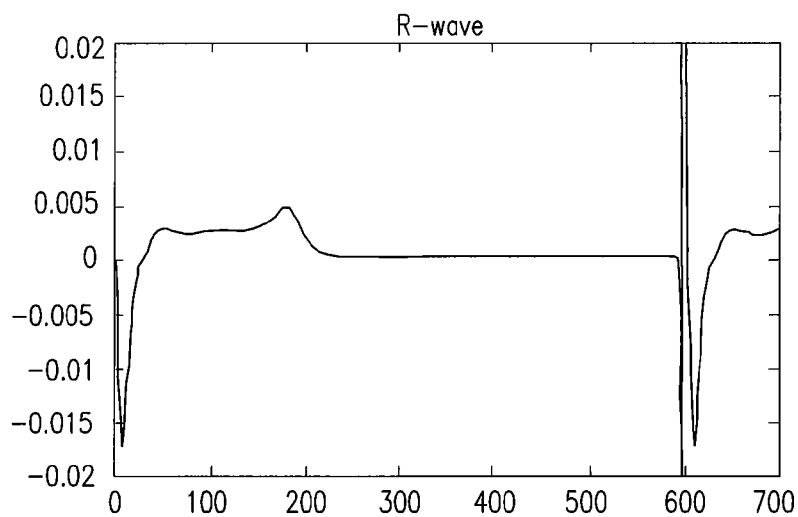

As discussed above, the heart performance criteria may be stroke volume which can include a determination of the integrated ensemble averaging in order to provide an indication of the total volume of blood that is being pumped by the heart in response to stimulation at the selected location. With reference to FIGS. 7 and 8, in one exemplary calculation, stroke volume is proportional to the area under the peak portion 710, 810 of the impedance derivative (dZ/dt) curve between respective bounding point pairs 720/730, 820/830. In one case, the first bounding point 720, 820 may be the point on the dZ/dt curve corresponding to the most positive point 740, 840 on the impedance curve Z and the second bounding point 730, 830 may be the point on the dZ/dt curve corresponding to the intersection of a line 745, 845 between the upward peak 750, 850 immediately preceding the most positive downward peak 760, 860 and the dZ/dt curve. Based on the impedance measurements and corresponding stroke volume calculations of FIGS. 7 and 8, the stroke volume parameter indicated in FIG. 7B is greater than the stroke volume parameter indicated in FIG. 8B. Thus the stimulation electrode position corresponding to the impedance curve of FIG. 7 is more optimal than the stimulation electrode position of FIG. 8. Stroke volume is, however, only one of a number of different heart performance parameters that can be captured at implantation by obtaining the impedance measurements in the manner described above.

For example, other parameters, such as the time delay between the QRS peak and the maximum derivative of the admittance (Y=1/Z) can also be obtained. This measurement is indicative of the contractility of the heart which provides information about the isovolumic contraction type. When comparing respective time delays, a shorter time delay is considered hemodynamically beneficial relative to a longer time delay. This information can be used to select a stimulation electrode location that may result in increased synchrony between the heart chambers. With reference to FIGS. 7 and 8, respective time delays 770, 870 may be calculated between the QRS peak (which is at time zero on the graphs) and the maximum derivative 780, 880. From these calculations, the time delay of FIG. 7B, which is approximately 195 msec., is greater than the time delay of FIG. 8B, which is approximately 170 msec. Thus, if time delay is the performance criteria, the stimulation electrode position corresponding to the impedance curve of FIG. 8 is more optimal than the stimulation electrode position of FIG. 7.

A further parameter that can be obtained using the impedance measurement and the cardiac electrogram is the time between the minimum derivative of admittance and the QRS complex which provides a measure of the relaxation time. Yet a further metric is the time between the minimum and maximum derivatives of admittance which is related to the systolic time interval and is further indicative of synchrony.

From the above, it is noted that the determination of whether a particular performance criteria is satisfied may be based on a comparison of like criteria measurements obtained at different stimulation electrode positions. If a criteria measurement for a particular stimulation position is not better than the same criteria measurement for another stimulation position, then the performance criteria for the particular stimulation position would not be satisfied. However, if the criteria measurement for the particular stimulation position is better than the other stimulation position, then the performance criteria for the particular stimulation position would be satisfied. As evidenced by FIGS. 7 and 8, depending on the criteria selected, e.g., stroke volume or time delay, the determined optimal stimulation electrode position may be different.

It will be appreciated that each of the leads of a multi-lead system can be assessed in the above-described manner so that the overall performance of the implanted device can be optimized or at least result in performance that meets a selected criteria. It will be further appreciated that the information about the heart's performance parameter gathered in the above-described manner can be used not only to select a desired implantation location, but also to adjust other parameters of the implanted device. For example, this information may also be used to optimize AV and V-V timing at implant by changing the associated delays. It will be appreciated that any of a number of different uses can be made of the captured impedance information when implanting a cardiac stimulation device without departing from the spirit of the present invention.

Although the above-disclosed embodiments have shown, described and pointed out the novel features of the invention as applied to the above-disclosed embodiments, it should be understood that various omissions, substitutions, and changes in the form of the detail of the device, systems and methods shown may be made by those skilled in the art without departing from the scope of the present invention. Consequently, the scope of the invention should not be limited to the foregoing description, but should be defined by the appended claims.

What is claimed is:

1. A method of assessing bi-ventricular pacing efficacy during implant of pacing leads, said method comprising:
    delivering bi-ventricular stimulation pulses to a patient's heart through a left-ventricular (LV) electrode and a right-ventricular (RV) electrode;

obtaining impedance measurements of the transthoracic cavity of the patient while the bi-ventricular stimulation pulses are being delivered using an impedance sensing vector that does not include either of the LV electrode and the RV electrode;

processing the impedance measurements to ascertain whether a heart performance parameter satisfies a criteria; and if the heart performance parameter does not satisfy the criteria, repositioning at least one of the LV electrode and the RV electrode and repeating the delivering, obtaining and processing, until the heart performance parameter satisfies the criteria.

2. The method of claim 1, wherein the impedance sensing vector is defined by one or more of internal electrodes and external electrodes.

3. The method of claim 2, wherein the impedance sensing vector is defined by a pair of internal electrodes.

4. The method of claim 2, wherein the impedance sensing vector is defined by a pair of external electrodes.

5. The method of claim 2, wherein the impedance sensing vector is defined by an internal electrode and an external electrode.

6. A method of assessing bi-ventricular pacing efficacy during implant of pacing leads, said method comprising:
   delivering bi-ventricular stimulation pulses to a patient's heart through a first left-ventricular (LV) electrode placed at a first LV location and a first right-ventricular (RV) electrode placed at a first RV location;
   obtaining impedance measurements of the transthoracic cavity of the patient while the bi-ventricular stimulation pulses are being delivered using an impedance sensing vector that does not include either of the first LV electrode and the first RV electrode; and
   processing the impedance measurements to ascertain whether a heart performance parameter satisfies a criteria;
   when the heart performance parameter does not satisfy the criteria, delivering additional bi-ventricular stimulation pulses to the heart through any one of:
      a second LV electrode placed at a second LV location and the first RV electrode placed at the first RV location,
      the first LV electrode placed at the first LV location and a second RV electrode placed at a second RV location, and
      a second LV electrode placed at a second LV location and a second RV electrode placed at a second RV location,
   obtaining additional impedance measurements of the transthoracic cavity of the patient while the additional bi-ventricular stimulation pulses are being delivered using an impedance sensing vector that does not include any electrode that is used to deliver stimulation pulses; and
   processing the additional impedance measurements to ascertain whether a heart performance parameter satisfies a criteria.

7. A method of assessing bi-ventricular pacing efficacy during implant of pacing leads, said method comprising:
   delivering bi-ventricular stimulation pulses to a patient's heart through a left-ventricular (LV) electrode placed at a LV location and a right-ventricular (RV) electrode placed at a RV location;
   obtaining impedance measurements of the transthoracic cavity of the patient while the bi-ventricular stimulation pulses are being delivered using an impedance sensing vector that does not include either of the LV electrode and the RV electrode; and
   processing the impedance measurements to ascertain whether a heart performance parameter satisfies a criteria;
   wherein processing the impedance measurements to ascertain whether the heart performance parameter satisfies a first criteria comprises:
   obtaining multiple impedance measurements;
   determining the heart performance parameter based on an average impedance parameter from the multiple impedance measurements;
   evaluating the average impedance parameter to ascertain whether the first criteria is satisfied.

8. The method of claim 7, wherein the heart performance parameter corresponds to stroke volume.

9. The method of claim 8, wherein the stroke volume is determined by ensemble averaging and integrating the multiple impedance measurements.

10. A method of assessing bi-ventricular pacing efficacy during implant of pacing leads, said method comprising:
   delivering bi-ventricular stimulation pulses to a patient's heart through a left-ventricular (LV) electrode placed at a LV location and a right-ventricular (RV) electrode placed at a RV location;
   obtaining impedance measurements of the transthoracic cavity of the patient while the bi-ventricular stimulation pulses are being delivered using an impedance sensing vector that does not include either of the LV electrode and the RV electrode;
   capturing electrogram signals of the heart during bi-ventricular pacing; and
   processing the impedance measurements to ascertain whether a heart performance parameter satisfies a criteria;
   wherein processing the impedance measurements comprises processing the electrograms and impedance measurements to assess the performance parameter of the heart.

11. The method of claim 10, wherein processing the electrogram and impedance measurement comprises evaluating the time delay between QRS peak and the maximum derivative of admittance corresponding to the impedance.

12. The method of claim 10 wherein processing the electrogram and impedance measurement comprises evaluating the time between the minimum derivative of admittance corresponding to the impedance and the QRS peak.

13. The method of claim 1 wherein processing the impedance measurements comprises evaluating the time between the minimum and the maximum derivatives of admittance corresponding to the impedance.

14. A cardiac stimulation system comprising:
   a left-ventricular (LV) electrode adapted for placement at a LV location and a right-ventricular (RV) electrode adapted for placement at a RV location;
   a pulse generator; and
   a processor operative to:
      cause the pulse generator to deliver bi-ventricular stimulation pulses to the heart through the left-ventricular (LV) electrode and the right-ventricular (RV) electrode;
      obtain multiple impedance measurements of the transthoracic cavity of the patient while bi-ventricular stimulation pulses are being delivered using an impedance sensing vector that does not include either of the LV electrode and the RV electrode;

determine a heart performance parameter based on an average impedance parameter from the multiple impedance measurements; and.

evaluate the average impedance parameter to ascertain whether a criteria is satisfied.

15. A method of assessing pacing efficacy during implant of pacing leads, said method comprising:

delivering stimulation pulses to the heart through an electrode placed at a first location;

obtaining impedance measurements of the transthoracic cavity of the patient while stimulation pulses are being delivered using an impedance sensing vector that does not include the electrode used to deliver stimulation pulses;

processing the impedance measurements to ascertain whether a heart performance parameter satisfies a criteria; and if the heart performance parameter does not satisfy the criteria, positioning the electrode at a second location and repeating the delivering, obtaining and processing, until the heart performance parameter satisfies the criteria.

16. The method of claim 15 wherein positioning an electrode at a second location comprises moving the first electrode to the second location.

17. The method of claim 15 wherein positioning an electrode at a second location comprises selecting a second electrode for stimulation pulse delivery.

* * * * *